United States Patent
Kafka et al.

(10) Patent No.: US 8,902,939 B2
(45) Date of Patent: Dec. 2, 2014

(54) BROADLY TUNABLE OPTICAL PARAMETRIC OSCILLATOR

(75) Inventors: James D. Kafka, Palo Alto, CA (US); Ching-Yuan Chien, Palo Alto, CA (US); Yujun Deng, San Jose, CA (US); Andrei C. Florean, Menlo Park, CA (US); David E. Spence, San Jose, CA (US); Jianping Zhou, Palo Alto, CA (US)

(73) Assignee: Newport Corporation, Irvine, CA (US)

( * ) Notice: Subject to any disclaimer, the term of this patent is extended or adjusted under 35 U.S.C. 154(b) by 493 days.

(21) Appl. No.: 13/011,780

(22) Filed: Jan. 21, 2011

(65) Prior Publication Data

US 2011/0180729 A1     Jul. 28, 2011

Related U.S. Application Data

(60) Provisional application No. 61/336,499, filed on Jan. 22, 2010.

(51) Int. Cl.
| | |
|---|---|
| *H01S 3/10* | (2006.01) |
| *H01S 3/00* | (2006.01) |
| *G01N 21/35* | (2014.01) |
| *G01N 21/39* | (2006.01) |
| *H01S 3/108* | (2006.01) |
| *H01S 3/11* | (2006.01) |
| *G02F 1/39* | (2006.01) |

(52) U.S. Cl.
CPC .............. *H01S 3/005* (2013.01); *G01N 21/359* (2013.01); *G01N 21/39* (2013.01); *G01N 2021/399* (2013.01); *H01S 3/1118* (2013.01); *H01S 3/1083* (2013.01); *G02F 1/39* (2013.01); *H01S 3/0014* (2013.01)
USPC .............................................. 372/21; 372/20

(58) Field of Classification Search
CPC ..... H01S 3/005; H01S 3/0014; H01S 3/1118; H01S 3/1083; G02F 1/39; G02F 1/395
USPC ....................................................... 372/20, 21
See application file for complete search history.

(56) References Cited

U.S. PATENT DOCUMENTS

| | | |
|---|---|---|
| 3,662,183 A | 5/1972 | Ashkin |
| 5,017,806 A | 5/1991 | Edelstein |

(Continued)

OTHER PUBLICATIONS

Zhang, "High-repetition-rate Femtosecond Optical Parametric Oscillators Based on KTP and PPLN," 2002, Dissertation, Physics Department, Philipps University of Marburg.*

(Continued)

*Primary Examiner* — Julio J Maldonado
*Assistant Examiner* — Joshua King
(74) *Attorney, Agent, or Firm* — Brian F. Swienton

(57) ABSTRACT

A novel broadly tunable optical parametric oscillator is described for use in numerous applications including multi-photon microscopy. The optical parametric oscillator includes at least one sub-picosecond laser pump source configured to output a pump signal having a wavelength of about 650 nm or less and at least one type II optical parametric oscillator in optical communication with the pump source and configured to generate a single widely tunable pulsed optical signal. In one application, an optical system is in optical communication with the optical parametric oscillator and configured to direct at least a portion of the optical signal to a specimen, and at least one analyzing device is configured to receive a signal from the specimen in response to the optical signal.

18 Claims, 5 Drawing Sheets

(56) References Cited

U.S. PATENT DOCUMENTS

| | | | |
|---|---|---|---|
| 5,047,668 A * | 9/1991 | Bosenberg | 359/330 |
| 5,134,622 A | 7/1992 | Deacon | |
| 5,144,630 A | 9/1992 | Lin | |
| 5,159,487 A | 10/1992 | Geiger | |
| 5,195,104 A | 3/1993 | Geiger | |
| 5,206,868 A | 4/1993 | Deacon | |
| 5,291,503 A | 3/1994 | Geiger | |
| 5,296,960 A | 3/1994 | Ellingson | |
| 5,371,752 A | 12/1994 | Powers | |
| 5,457,707 A | 10/1995 | Sobey | |
| 5,521,390 A | 5/1996 | Sato | |
| 5,563,508 A | 10/1996 | Tatah | |
| 5,579,152 A | 11/1996 | Ellingson | |
| 5,606,453 A | 2/1997 | Walling | |
| 5,633,885 A | 5/1997 | Galvanauskas | |
| 5,742,626 A | 4/1998 | Mead | |
| 5,786,560 A | 7/1998 | Tatah | |
| 5,796,512 A | 8/1998 | Wachman | |
| 5,801,876 A | 9/1998 | Kouta | |
| 5,847,861 A | 12/1998 | Kafka | |
| 5,883,915 A | 3/1999 | Kortz | |
| 5,896,220 A | 4/1999 | Stamm | |
| 5,898,718 A | 4/1999 | Mohatt | |
| 6,002,697 A | 12/1999 | Govorkov | |
| 6,236,779 B1 * | 5/2001 | Kafka et al. | 385/31 |
| 6,373,869 B1 * | 4/2002 | Jacob | 372/22 |
| 6,389,198 B2 | 5/2002 | Kafka | |
| 6,594,301 B2 | 7/2003 | Pang | |
| 6,608,852 B2 | 8/2003 | Govorkov | |
| 6,614,584 B1 | 9/2003 | Govorkov | |
| 6,650,682 B1 | 11/2003 | Jones | |
| 6,731,660 B2 | 5/2004 | Arbore et al. | |
| 6,768,576 B2 | 7/2004 | Caudle | |
| 6,798,804 B2 | 9/2004 | Hayakawa | |
| 6,834,066 B2 | 12/2004 | Bragin | |
| 6,862,307 B2 | 3/2005 | Osmanow | |
| 7,088,749 B2 | 8/2006 | Nakayama | |
| 7,248,608 B2 | 7/2007 | Nettleton | |
| 7,440,176 B2 | 10/2008 | Fidric | |
| 7,680,170 B2 | 3/2010 | Hu | |
| 7,830,608 B2 | 11/2010 | Hu | |
| 2002/0185478 A1 * | 12/2002 | Kafka et al. | 219/121.68 |
| 2003/0008448 A1 * | 1/2003 | Kafka et al. | 438/200 |
| 2003/0137719 A1 * | 7/2003 | Van Der Veer | 359/330 |
| 2004/0252300 A1 * | 12/2004 | Slater | 356/318 |
| 2005/0094679 A1 * | 5/2005 | Kafka et al. | 372/18 |
| 2005/0243876 A1 | 11/2005 | Kung | |
| 2007/0035810 A1 | 2/2007 | Henderson | |

OTHER PUBLICATIONS

Laenen et al., "Parametric Generation of Synchronized, Independently Tunable Subpicosecond Pulses in the Midinfrared with Adjustable Pulse Duration," Mar. 1998, J. Opt. Soc. Am. B., 15, 3, 1213-1217.*

Reed et al., "Widely Tunable Femtosecond Optical Parametric Amplifier at 250 kHz with a Ti:Sapphire Regenerative Amplifier," Nov. 15, 1994, Optics Letters, 19, 22, 1855-1857.*

C. Cleff et al., "Femtosecond OPO based on LBO pumped by a frequency-doubled Yb-fiber laser-amplifier system for CARS spectroscopy," Apllied Physics, vol. 103, p. 795-800, 2011.

T. Lang et al., "Rapidly Spectral Ramping of an ultra-wide Tuneable Femtosecond Non-collinear Optical Parametric Oscillator (NOPO) with high average output power," Lasers, Sources, and Related Photonics Devices Technical Digest, 2012.

Min et al., "Imaging chromophores with undetectable fluorescence by stimulated emission microscopy," Nature, vol. 4, p. 1105-1109, Oct. 22, 2009.

Min et al., "Imaging chromophores with undetectable fluorescence by stimulated emission microscopy," Nature, vol. 4, p. 1105-1109, Oct. 22, 2009, Supplemental Information.

"Levante Emerald Femtosecond Version" Laser System Datasheet, APE GmbH, 2009.

Wu et al., "Simple, high-performance type II β-BaB4O2 optical parametric oscillator," Applied Optics, vol. 36, No. 24, p. 5898-5901, Aug. 20, 1997.

Vodopyanov et al., "ZnGeP2 optical parametric oscillator with 3.8-12.4-μm tunability," Optics Letters, vol. 25, No. 11, p. 841-843, Jun. 1, 2000.

Komine, "Average-power scaling for ultraviolet-pumped β-barium borate and lithium triborate optical parametric oscillators," Optical Society of America, vol. 10, No. 9, p. 1751-1757, Sep. 1993.

W.R. Bosenberg et al., "Type II phase matching in a β-barium borate optical parametric oscillator," Applied Physics Letters, vol. 56, No. 19, p. 1819-1821, May 7, 1990.

C. Fabre et al., "Theoretical analysis of self-phase locking in a type II phase-matched optical parametric oscillator," Optical Communications, vol. 170, p. 299-307, Nov. 1, 1999.

K. Wolfrum et al., "intense bandwidth- and diffraction-limited picosecond pulses with a large tuning range," Optical Communications, vol. 97, No. 1, p. 41-46, Mar. 1, 1993.

M. Ghotbi et al., "Ti:sapphire-Pumped Infrared Femtosecond Optical Parametric Oscillator Based on BiB3O6," Optical Society of America, 2007.

P.E.Powers et al., "High-repetition rate femtosecond optical parametric oscillator based on CsTiOAsO4," Optics Letters, vol. 19, No. 1, p. 37-39, Jan. 1, 1994.

G.M. Gale et al., "Sub-20-fs tunable pulses in the visible from an 82-MHz optical parametric oscillator," Optics Letters, vol. 20, No. 14, p. 1562-1564, Jul. 15, 1995.

* cited by examiner

BROADLY TUNABLE OPTICAL PARAMETRIC OSCILLATOR

CROSS-REFERENCE TO RELATED APPLICATIONS

The present application claims priority to U.S. Patent Application Ser. No. 61/336,499, filed on Jan. 22, 2010, the contents of which are hereby incorporated by reference in its entirety herein.

BACKGROUND

Tunable optical sources of ultrafast pulses have found increasing use in physics, chemistry and biology. For almost two decades the most popular tunable optical source of ultrafast pulses has been the Titanium doped Sapphire or Ti:sapphire laser. This laser source possesses a combination of high average power, short pulses, and reasonably broad tunability. Typical Ti:sapphire lasers can produce about 1 W to about 4 W of average power with pulse durations on the order of 100 fs. Both picosecond pulses as well as much shorter pulses at lower power have also been demonstrated. The tuning range can extend from about 680 nm to about 1080 nm although with significantly less than about 1 W average power available at the edges of the tuning range.

During the last decade Ti:sapphire lasers and optical sources that pump Ti:sapphire lasers have been combined into a single box and engineered to produce a hands-off, fully automated tunable laser system. The advent of these user-friendly tunable ultrafast one-box laser systems has greatly broadened the number of applications accessible for these lasers. In particular, applications in biology and bio-chemistry have been well served by these sources. For example, multi-photon microscopy (MPM) uses both an ultrafast laser and a microscope to examine a specimen or sample.

In multi-photon microscopy an ultrafast source of near infrared (IR) light is used to excite the sample rather than the continuous wave (cw) source of visible light that is used in single photon systems. The samples under investigation are excited not by one photon of visible light but rather by two (or more) photons from the ultrafast near IR source. Only the portions of the sample that are at the focus of the laser beam are subject to optical radiation having sufficient intensity to experience the two photon excitation. When this portion of the sample is doped with a fluorescent dye, all the fluorescence is emitted from the small volume of the sample that is excited. For example, U.S. Pat. No. 5,034,613 issued to Denk et al., which is incorporated by reference in its entirety herein, describes a two-photon laser microscope. Advantages of this technique include improved spatial resolution, and "optical sectioning" of the sample since the excited volume extends only over a small depth in the sample. The use of the near IR wavelengths is also desirable for extended lifetime of living samples relative to visible excitation.

The popularity of tunable ultrafast sources for this application is due to the fact that many biological samples do not fluoresce on their own. As such, dyes are used to stain portions of the sample. Presently, there are dozens of dyes available depending on the sample that is to be investigated. Further, each dye has its own wavelength of optimal two-photon absorption. Thus, a tunable optical source allows great flexibility in what dyes may be used, and thus, what types of samples can be investigated.

Typically, the microscope includes a number of lenses made of glass and often at least one acousto-optic modulator for modulating the laser beam. As the ultrafast laser pulses pass through these materials, the pulse duration increases due to the dispersion. As a result, the optical signal may be temporally broadened, often by a factor of 2 or 3. This material dispersion can be pre-compensated for by placing a pair of prisms between the laser and the microscope in an appropriate configuration. Further, this dispersion compensation allows for 100 fs pulses to be incident directly on the sample. Recently, automated prism pairs have been added to the aforementioned one-box ultrafast laser systems. During use the user tunes the laser through a computer interface. In response, the laser adjusts both the wavelength and the position or orientation of the prism pair to maintain the shortest pulse at the sample.

One of the limits of MPM is that the depth of penetration of the light into the sample is restricted, often to only tens of microns. In biological samples, scattering of the fluorescence emitted by the excited portion of the sample is the limiting factor. This scattering decreases at longer wavelengths however and, thus, longer wavelength ultrafast sources can lead to greater penetration depth. There are a number of additional limits to longer wavelength excitation. For example, currently most microscopes have increasingly large losses due to the coatings on their optics at wavelengths longer than about 1300 nm. Further, typically in most biological samples there is a strong absorption due to water near 1400 nm.

Thus, it is desirable to have an ultrafast source that tunes not just from about 680 nm to about 1080 nm as the Ti:sapphire laser does, but from about 650 nm to about 1400 nm. A combination of sources has been demonstrated to cover this entire range. If the output of the Ti:sapphire laser is used to pump an optical parametric oscillator (OPO), the OPO can cover the missing wavelength range from 1080 nm to 1400 nm. Ti:sapphire pumped OPOs using KTP, RTP or CTA have been demonstrated to cover most of this wavelength range from about 1050 nm to 1330 nm. These OPOs typically produce average powers of a few hundred mW and pulse durations of 200 fs. In combination with the Ti:sapphire laser that is output from a separate port, most of the tuning range can be covered.

More recently OPOs using a periodically poled Lithium Niobate (PPLN) crystal have been demonstrated. Translating the PPLN, which typically contains a fan-shaped grating, provides tuning of the OPO. In combination with tuning the pump laser, a tuning range that covers from 1000 nm to 1600 nm with no wavelength gaps has been demonstrated. The OPO requires mirrors with high reflectivity over this entire tuning range in order to avoid having to manually replace mirrors in the middle of the tuning range. Again, in combination with the Ti:sapphire laser that is output from a separate port, all of the tuning range from 650 nm to beyond 1400 nm can be covered. Because the output of the Ti:sapphire and the OPO come from different output ports, fully automated tuning of the system with a single beam and with dispersion compensation has not yet been demonstrated.

Another alternative to cover the entire tuning range desired for MPM would be to use a shorter wavelength pump laser. Very recently an ultrafast source at 1045 nm was frequency doubled to produce ultrafast pulses in the green at 523 nm. The frequency doubled pump source was used to pump an OPO with a Type 1 BBO crystal and a tuning range of 690 nm to 980 nm was demonstrated for the signal wavelength with pulse durations of 300 fs. Idler wavelengths that covered the range from 1120 nm to >2000 nm were output from a second port. This system has a gap in the tuning range due to the degeneracy of the OPO at 1045 nm.

Thus, there is an ongoing need for a source of ultrafast pulses with an extremely broad tuning range with high average power and 100 fs pulses both for MPM and other applications. There is a further ongoing need for this tunable ultrafast source to cover the range from 680 nm to 1380 nm in and be fully automated. In addition, there is yet a further need for this automated source of ultrafast pulses to have a single output port. Lastly, there is yet another need to couple this single port ultrafast source with a fully automated dispersion compensation device.

SUMMARY

The present application is directed to a novel broadly tunable optical parametric oscillator and method of manufacture. More specifically, the various embodiments of the novel optical parametric oscillators disclosed herein provide a broadly tunable ultrafast laser system configured for use in a variety of applications.

In one embodiment, the present application discloses a laser system which includes at least one sub-picosecond laser pump source configured to output at least one pump signal having a wavelength of about 650 nm or less, at least one type II optical parametric oscillator in optical communication with the pump source and configured to generate a single pulsed optical signal, at least one optical system in optical communication with the optical parametric oscillator and configured to direct at least a portion of the optical signal to a specimen, and at least one analyzing device configured to receive at least one specimen signal from the specimen in response to the optical signal.

In another embodiment, the present application discloses an ultrafast laser source and includes a sub-picosecond oscillator configured to generate an optical signal continuously tunable from about 650 nm to about 1400 nm with the output emitted from a single output port, an optical system in optical communication with the sub-picosecond source and configured to direct the optical signal through the output port to a specimen, and at least one analyzing device configured to receive at least one specimen signal from the specimen in response to the optical signal.

In another embodiment, the present application is directed to a laser system which includes at least one picosecond laser pump source configured to output at least one pump signal having a wavelength of about 650 nm or less, a type II optical parametric oscillator in optical communication with the pump source and configured to generate a single optical signal, an optical system in optical communication with the optical parametric oscillator and configured to direct at least a portion of the optical signal to a specimen, and at least one analyzing device configured to receive at least one specimen signal from the specimen in response to the optical signal.

Other features and advantages of the embodiments of the various novel broadly tunable optical parametric oscillators as disclosed herein will become apparent from a consideration of the following detailed description.

BRIEF DESCRIPTION OF THE DRAWINGS

Various embodiments of a novel broadly tunable optical parametric oscillator will be explained in more detail by way of the accompanying drawings, wherein.

DETAILED DESCRIPTION

Figure 1:
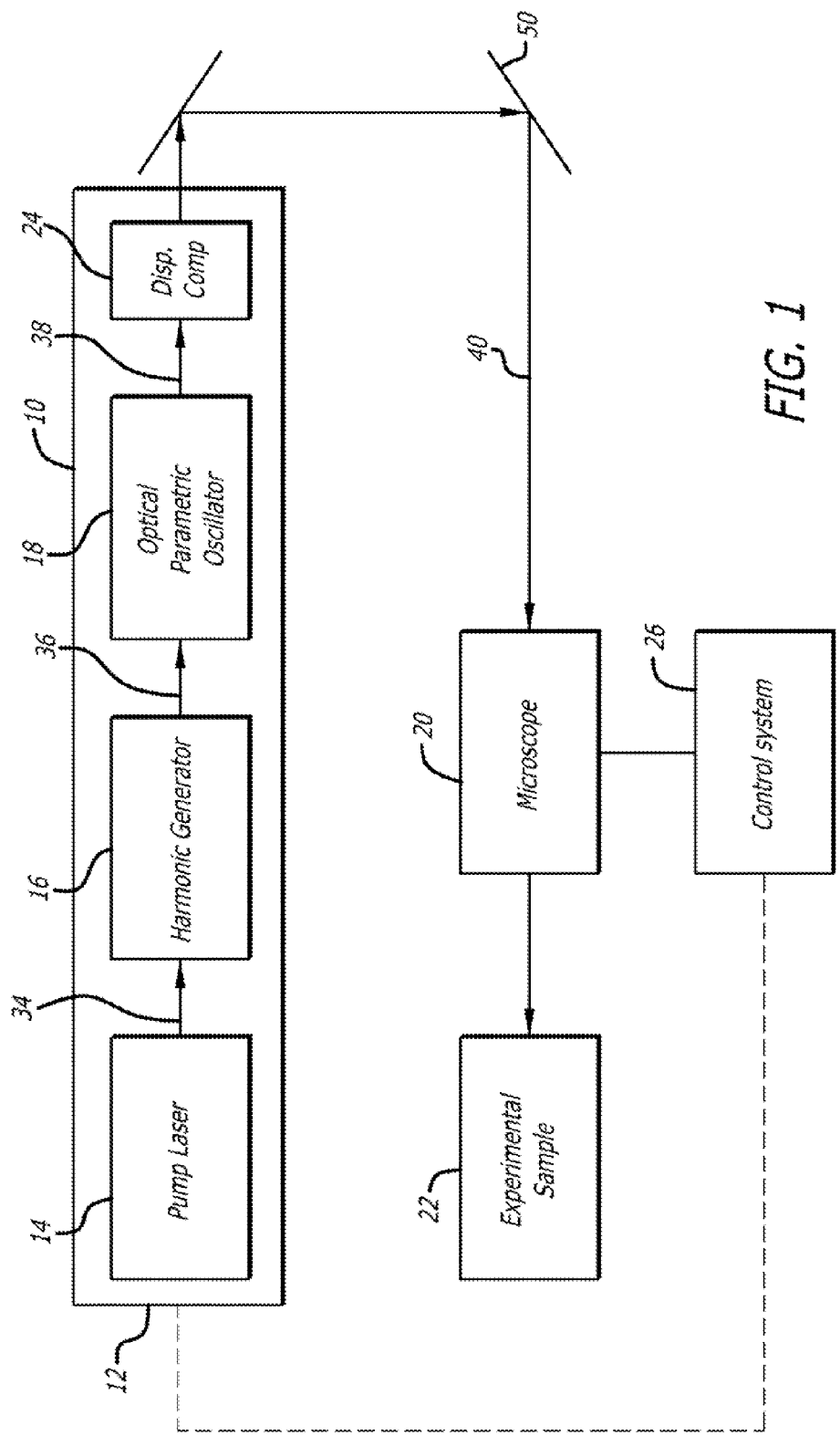
FIG. 1 shows a schematic diagram of an embodiment of a broadly tunable ultrafast laser system coupled to an optical system for examining an experimental sample.

FIG. 1 shows a block diagram of an embodiment of a broadly tunable ultrafast laser system. In the illustrated embodiment, the broadly tunable ultrafast laser system 10 includes a housing 12 containing at least one pump laser 14 configured as a pump source, at least one harmonic generator 16, and at least one optical parametric oscillator 18. In one embodiment for use in multiple photon microscopy systems, the broadly tunable ultrafast laser system 10 may be optically coupled to one or more microscopes or optical systems 20 for examining one or more experimental samples 22. In the illustrated embodiment, at least one dispersion compensator 24 is positioned within the broadly tunable ultrafast laser system housing 10. Optionally, the dispersion compensator 24 may be positioned between the broadly tunable ultrafast laser system housing 10 and the microscope 20. Further, the system shown in FIG. 1 may be operated without a dispersion compensator 24. In addition, one or more control or analyzing systems 26 may be in communication with at least one of the microscope 20, sample 22, dispersion compensator 24, or broadly tunable ultrafast laser system 10. The various components forming the broadly tunable ultrafast laser system will be described in greater detail below.

Figure 2:
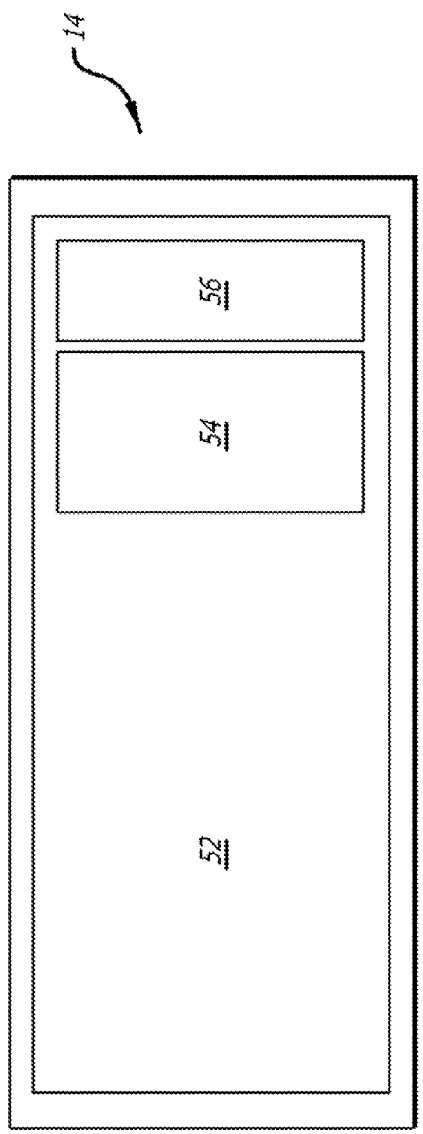
FIG. 2 shows a schematic diagram of an embodiment of a pump laser for use in providing a pump signal to the broadly tunable ultrafast laser system shown in FIG. 1.

Referring to FIGS. 1 and 2, the pump laser 14 is configured to provide a pump signal 34 to the harmonic generator 16. In one embodiment, the pump laser comprises an ultrafast laser system configured to provide sub-picosecond pulses of pump light to the harmonic generator 16. In another embodiment, the pump laser 14 may be configured to provide femtosecond pulses of pump light to the harmonic generator 16. In one embodiment, the pump laser 14 is configured to output an optical signal having a wavelength of about 500 nm to about 1800 nm. In another embodiment, the pump laser 14 is configured to output an optical signal 34 having a wavelength of less than about 650 nm. As such, the pump laser 14 may include at least one harmonic generator 16 therein. As such, the harmonic generator 16 may be positioned within the pump laser 14 or may be separate element in optical communication with the pump laser 14.

Those skilled in the art will appreciate that any variety of laser devices may be used as the pump laser 14, including, without limitations, diode pumped solid state lasers, bulk lasers, fiber lasers, fiber amplified bulk lasers, fiber amplifiers, disk lasers, and infrared laser devices. Referring again to FIGS. 1 and 2, in one embodiment the pump laser 14 comprises a mode-locked diode-pumped source 52 and a solid-state gain media 54. Optionally, the gain media 54 may have sufficient bandwidth to be capable of generating pulses of about 100 fs to about 300 fs in duration. Further, the gain media 54 may have sufficiently high thermal conductivity to allow high average powers to be generated. In one embodiment, the average power is about 10 W to about 20 W. In another embodiment, the average power is from about 20 W to about 40 W. Those skilled in the art will appreciate that the average power may be scalable as the technology evolves. Any variety of materials may be used to form the gain media 54, including, without limitations, Yb:YAG, Yb:KYW, Yb:KGW, Yb:glass, and Nd:glass. For example, in one embodiment, Yb-doped materials are used to form the gain media 54. As such, diodes with high brightness may be used to exceed the transparency level for these quasi-3 level gain media. Those skilled in the art will appreciate that any variety of sources may be used as a pump source 14 in the broadly tunable ultrafast laser system 10. In one embodiment, two fiber coupled pump sources producing about 25 W to about 100 W each are used to pump each of two sides of the gain media. Optionally, multiple fiber coupled pump sources may be configured to pump a single side of the gain media.

As shown in FIG. 2, the pump laser 14 may include one or more dispersion compensation devices 56 therein configured to enable the pump laser 14 to emit short optical pulses. In one embodiment, the optical pulses have pulse durations of about 100 fs to about 300 fs. Optionally, the pulse duration may last longer than about 300 fs. In another embodiment, the pulse duration is about 25 fs to about 100 fs. Exemplary dispersion compensation devices 56 comprise chirped mirrors. In another embodiment, the dispersion compensation device 56 is comprised of intracavity prisms pairs. Optionally, the pump laser 14 may be manufactured without a dispersion compensation device 56 therein. Further, the pump laser 14 may comprise a mode-locked laser system. Optionally, semiconductor saturable absorbers can be used to start and to stabilize the mode-locking of the pump source 14. Semiconductor saturable absorbers that may contain multiple quantum wells and anti-reflection coatings to increase the modulation depth are advantageous for obtaining the maximum power from the oscillator. Alternatively, Kerr lens mode-locking (KLM) can be used as the modelocking technique. In one embodiment, the maximum useful power of the pump source 14 may be limited by multi-pulsing of the oscillator or cw breakthrough as observed by measuring the spectrum dependent on the intracavity dispersion. In some embodiments, some performance characteristics may be dependent on the third order dispersion, the cavity alignment (particularly in the case of KLM), the properties of the mode locking device (such as the modulation depth of the SESAM) and/or the transmission of the output coupler of the pump laser 14. In one embodiment, the output coupler of the pump laser 14 has a transmission from about 5% to about 60%. In another embodiment, the output coupler of the pump laser 14 has a transmission of about 10% to about 40%. Optionally, the output coupler of the pump laser 14 may have a transmission of about 15% to about 35%.

In an alternate embodiment, the pump source 14 comprises a mode-locked infrared pump laser which includes at least one lower power diode-pumped solid-state source 52 and at least one fiber amplifier. Such a source is described in Y. Deng et al., *Optics Letters* Vol. 34, Iss. 22, pp. 3469-3471 (2009), the entire contents of which are hereby incorporated by reference herein. The laser system disclosed in Deng et al. produced about 18 W of power with pulse durations as short as about 50 fs. In another embodiment, at least one high power diode-pumped fiber oscillator may be used as the mode-locked infrared pump laser 14. Such a source is described in K. Kieu et al., *Office Letter's*, Vol. 34, Iss. 5, pp. 593-595, the contents of which are hereby incorporated by reference in their entirety. As such, a source similar to the device described in Kieu may be scaled to higher average powers using large mode area fibers, photonic crystal fibers, chirally coupled core fibers and the like. Optionally, the pump laser 14 may include various optical devices, lenses, gratings, filters, polarizers, Q-switches, acousto-optical devices, dispersion compensators, and the like therein.

The pump laser 14 may be configured to output at least one pump signal 34. In one embodiment, the pump signal 34 may have a wavelength from about 500 nm to about 1800 nm. For example, in one embodiment, the pump signal 34 has a wavelength of about 1040 nm. Optionally, as shown in FIG. 1, frequency doubling of the typical output wavelength (between about 950 nm and about 1200 nm) of the pump laser 14 via the harmonic generator 16 may be necessary to achieve a pump signal 34 wavelength of about 475 nm to about 600 nm. As such, frequency doubling crystals including LBO, BBO and/or BiBO may be used in the harmonic generator 16 with conversion efficiencies as high as 70% to 80%, although those skilled in the art will appreciate that the present system may be configured to operate with lower conversion efficiencies. Further, the crystal thickness and focusing may be optimized for conversion efficiency, pulse duration and beam quality or any combination thereof. In another embodiment, periodically poled crystals such as Periodically Poled Lithium Niobate (PPLN), Periodically Poled Stoichiometric Lithium Tantalate (PPSLT) and Periodically Poled Potassium Titanyl Phosphate (PPKTP) may also be used within the harmonic generator 16. For example, in one embodiment during use, the harmonic generator 16 may output at least one optical signal 36 of about 7 W having a wavelength of about 500 nm to about 750 nm without significant pulse broadening when pumped with an infrared pump signal 34 having about 10W of average power and 200 fs pulses. In one specific embodiment, the harmonic generator 16 may output at least one optical signal 36 of about 7 W having a wavelength of about 520 nm without significant pulse broadening when pumped with an infrared pump signal 34 having about 10 W of average power and 200 fs pulses. In the illustrated embodiment, the harmonic generator 16 is located between the pump laser 14 and the optical parametric oscillator 18. Optionally, the harmonic generator 16 may be positioned within the pump laser 14 or the optical parametric oscillator 18. In another embodiment, the harmonic generator 16 may be replaced with a harmonic generator configured to output third, fourth, fifth or greater harmonics of an input signal. Further, the broadly tunable ultrafast laser system may be operated without a harmonic generator 16.

Figure 3:
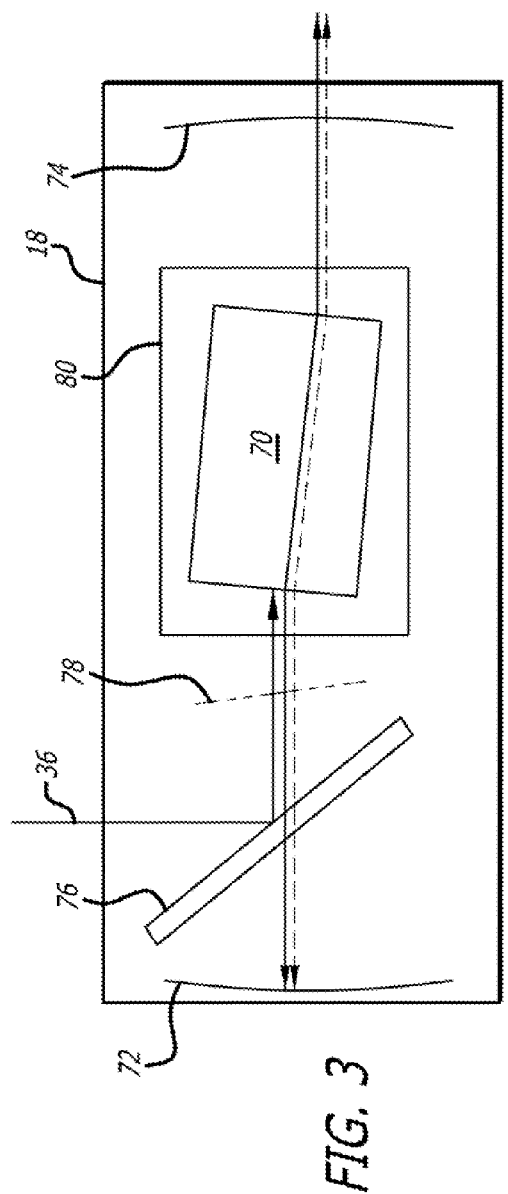
FIG. 3 shows a schematic diagram of an embodiment of an optical parametric oscillator for use in the broadly tunable ultrafast laser system.

As shown in FIG. 1, the optical signals 36 from the second harmonic generator 16 are used to pump at least one optical parametric oscillator 18 (OPO). In one embodiment, the OPO 18 comprises a sub-picosecond oscillator. In another embodiment, the OPO 18 comprises a picosecond oscillator. FIG. 3 shows an embodiment of an OPO 18 which may be used with the ultrafast laser system 10. In the illustrated embodiment, the OPO 18 includes an optical crystal 70 positioned on at least one component positioning system 80. In one embodiment, the component positioning system 80 is capable of controllably moving, rotating, of otherwise repositioning within the OPO 18. As such, the component positioning system 80 may be in communication with at least one controller. For example, the component positioning system 80 may be in communication with the control system 26.

Referring again to FIGS. 1 and 3, the OPO 18 may include multiple reflectors or mirrors forming an optical cavity. In the illustrated embodiment, a first reflector 72 and second reflector 74 may be configured to define a cavity. Optionally, at least one of the first reflector 72 and second reflector 74 comprises a broadband reflector. In the illustrated embodiment, the first reflector 72 acts as a high reflectance mirror having a reflectance of greater than 98% at a desired wavelength. In contrast, the second reflector 74 may act as an output coupler and have a reflectance of about 40% to about 90%. In another embodiment, the second reflector or output coupler 74 have a reflectance of about 60% to about 98%. In the illustrated embodiment, the first reflector 72 and second reflector 74 comprise curved reflectors although those skilled in the art will appreciate that any reflecting devices may be used. In addition, the OPO 18 may include one or more additional optical components 76, 78, such as various optical crystals, lenses, chirped mirrors, output couplers, prisms, semiconductor saturable absorbers, broadband mirrors, gratings, filters, polarizers, Q-switches, acousto-optical devices, dispersion compensators, glass plates, and the like. For example, in the illustrated embodiment, a pump signal reflector 76 and a glass plate 78 are positioned within the OPO 18. In another embodiment, the pump signal may be injected into the OPO 18 through the first reflector 72 or second reflector 74. Optionally, any component positioned within the OPO 18 may be positioned on or in communication with a selectively controllable component positioning system 80. Those skilled in the art will appreciate that any variety of OPO systems and/or crystals may be used to form the OPO 18. For example, the choice of OPO crystals 70 may include LBO, BBO, BiBO, PPLN, PPSLT, PPKTP, and $ZnGeP_2$.

Figure 4:
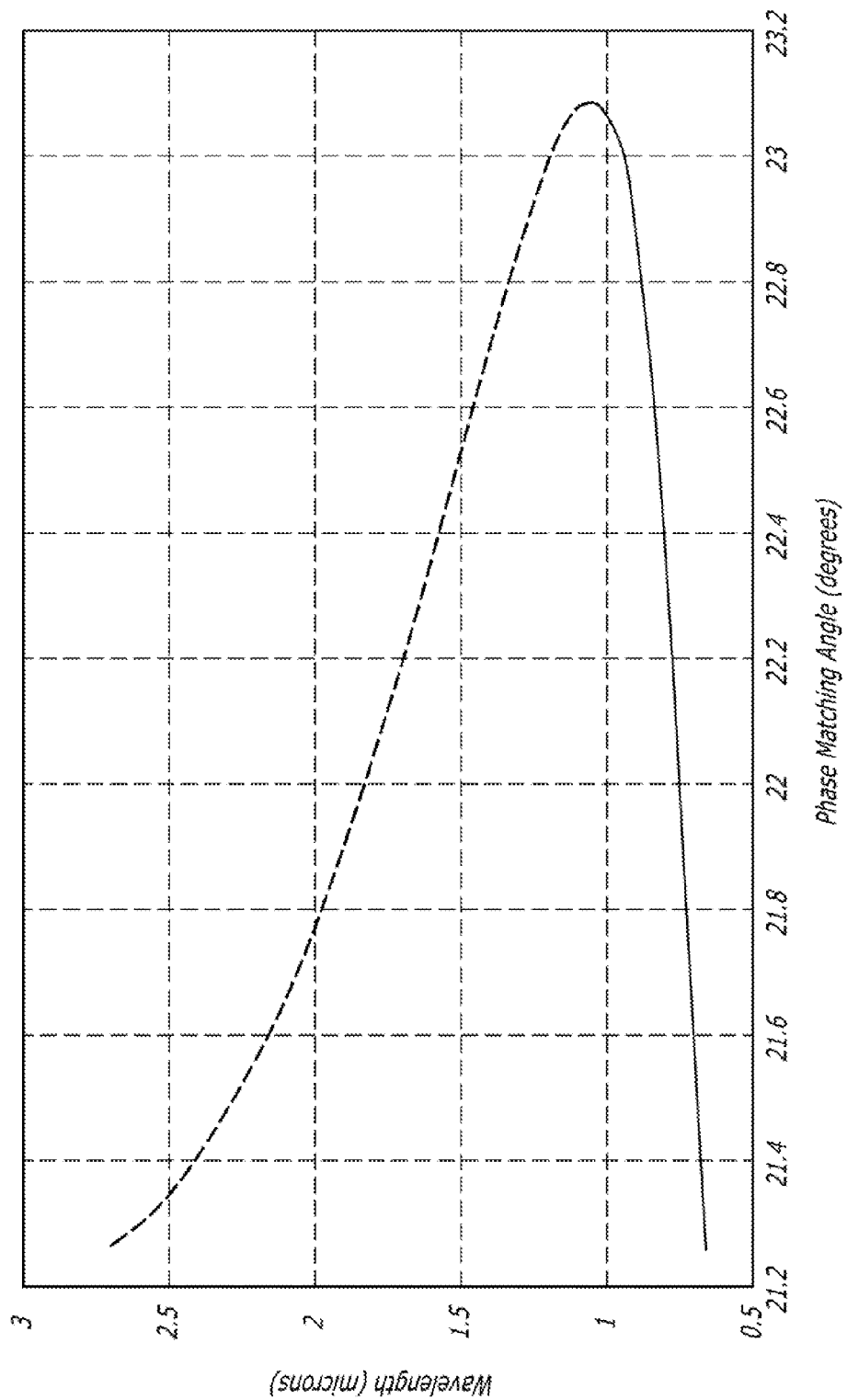
FIG. 4 shows graphically a phase matching curve of an embodiment of an optical parametric oscillator having a Type I optical crystal therein as used in an embodiment of a broadly tunable ultrafast laser system.

In one embodiment, the OPO 18 employs Type I phase matching. For example, a BBO-based OPO 18 may be pumped at about 520 nm. The Type I configuration offers both higher nonlinearity and a smaller range of angles needed to cover the tuning range. The phase matching curve for Type I BBO with 520 nm pump is shown in FIG. 4. The wavelengths of the signal pulses are shown by the solid line and the corresponding idler wavelengths are shown by the dotted line. Thus, at an angle of about 22 degrees the signal pulse has a wavelength of 730 nm and simultaneously an idler pulse with a wavelength of 1.8 microns is generated with the same polarization. As shown in FIG. 4, as the crystal 70 is tuned past 23 degrees the signal and the idler both approach a wavelength of 1040 nm, which is approximately twice the pump wavelength. The condition where the signal and idler have the same wavelength is called degeneracy. In a typical OPO 18, operating near degeneracy causes several problems. For example, the bandwidth of the pulses becomes quite large proximate to the region where the slope of the phase matching curve approaches infinity. Further, many different wavelengths can be generated at the same phase matching angle. This phenomenon may result in the generation of non-transform limited pulses.

In addition, the first reflector 72 and second reflector 74 of the OPO 18, which are typically configured to be highly reflective for the desired signal pulses, may also reflect the idler near degeneracy. As such, both the desired signal and idler may be resonated by the first reflector 72 and second reflector 74 in the OPO 18. This phenomenon is referred to as a doubly resonant OPO. In a doubly resonant OPO, the idler has two different paths to be generated. The first path arises each time the pump pulse amplifies the signal pulse in the crystal 70 and an idler pulse is created. The second arises when the idler from the previous round trip is captured by the first reflector 72 and second reflector 74 forming the OPO 18 and fed back to the crystal 70. These two paths may add up constructively or interfere depending on the phases of the idler from the two sources. Typically this interference leads to instability in the intensity of the idler and a modulation of the output spectrum with only small changes in the cavity length of the OPO 18. In response to this problem, the first reflector 72 and second reflector 74 forming the cavity of the OPO 18 may be configured to transmit the entire idler rather than reflect the idler back to the crystal 70, thus forming a singly resonant OPO 18. Unfortunately, presently the wavelength transition from highly reflecting to highly transmitting mirrors can not occur in less than about 40 nm. Thus, a tuning gap exists around degeneracy in all stable Type I OPOs.

Figure 5:
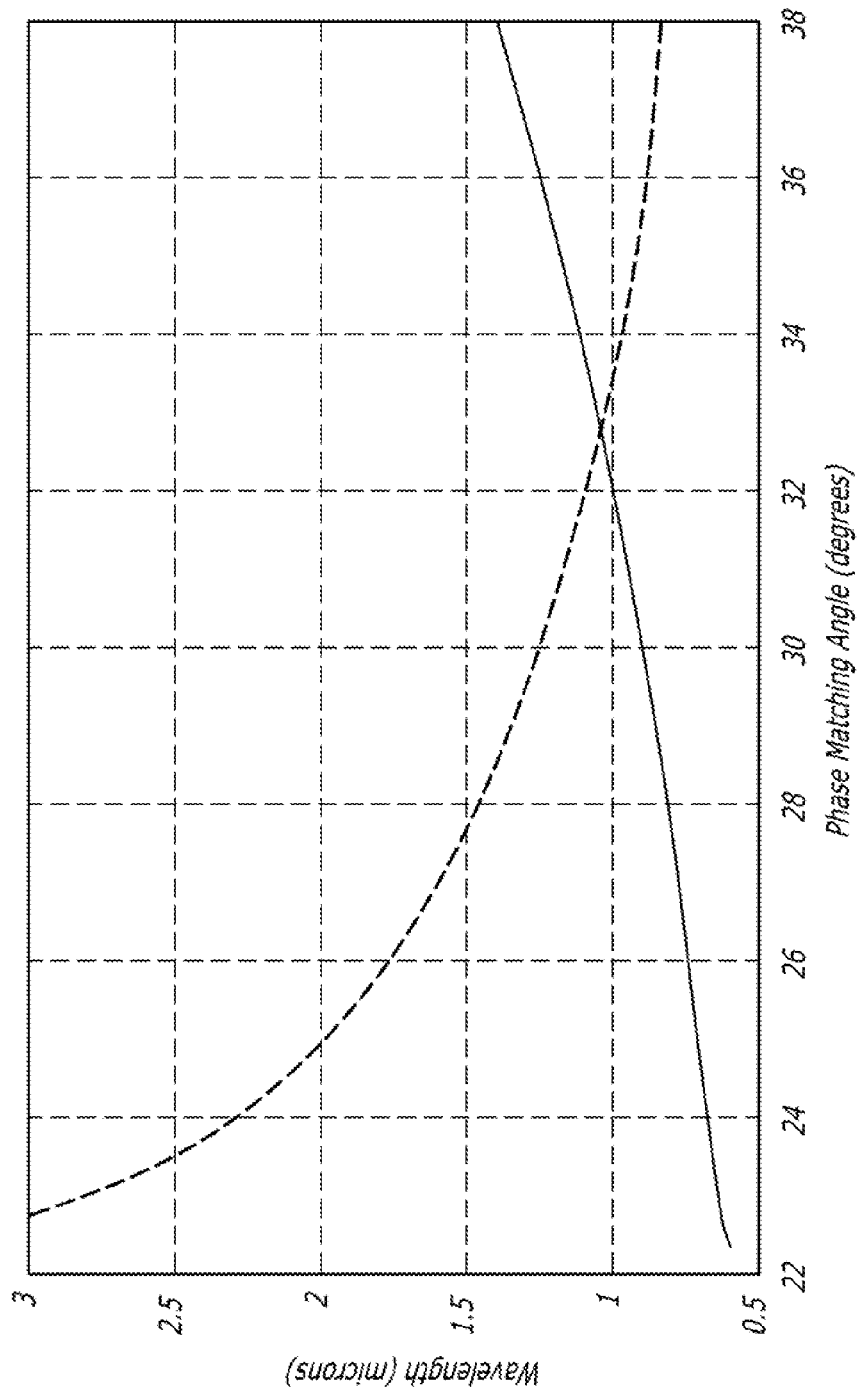
FIG. 5 shows graphically a phase matching curve of an embodiment of an optical parametric oscillator having a Type II optical crystal therein as used in an embodiment of a broadly tunable ultrafast laser system.

As such, in addition to a Type I OPO, the broadly tunable ultrafast laser system 10 may be configured to include one or more Type II OPOs 18. FIG. 5 shows the phase matching curve for a Type II BBO OPO 18 (See FIG. 1) pumped at 520 nm as a function of angle, although those skilled in the art will appreciate that any variety of Type II materials may be used. Exemplary Type II crystals include, without limitations, BBO, $KTiOPO_4$, LBO, $LiB_3O_5$, and $CsLiB_6O_{10}$. Again the signal is shown as the solid line and the idler which now has the opposite polarization is shown as the dotted line. As shown in FIG. 5, the slope of the phase matching curve never becomes infinite within the phase matching angle range. As such, the bandwidth never becomes excessively large, as opposed to the bandwidth of signals generated in a Type I configuration. At degeneracy, the signal and idler pulses will still have the same wavelength, similar to the Type I configuration detailed above. However, as the polarizations differ between the signal and the idler, the idler may be rejected either by inserting a polarization selector such as a polarizer, Brewster window, or similar optical element in the cavity or after the output coupler. In addition, the idler may be configured to experience a delay in one of the intracavity elements and, as such, experience a delay traversing the cavity of the OPO 18. As a result, both the insertion of a polarizer selector or delaying the idler within the cavity may produce a singly resonant OPO 18 with no tuning gap near degeneracy. As such, the tuning range is limited by the total bandwidth of the mirrors used, the phase matching range of the crystal, and/or the absorption of the idler pulses in the crystal at very long wavelengths, dependent on the crystal used. For example, BBO crystals may absorb the idler beyond 2.6 microns while other crystals such as Lithium Niobate can have low loss up to 5 microns.

Within the OPO 18, the idler has a lower output power and a larger tuning range than the signal. In a parametric process, energy is conserved and the energy of the signal photon plus the energy of the idler photon will be substantially equal to the energy of the pump photon. As shown in FIG. 4, as the signal tunes from about 650 nm to about 1400 nm the idler will tune from about 2600 nm to about 830 nm. Thus, the idler may be rejected from the cavity by a polarizer or similar device positioned within the OPO 18 or may be output from the output coupler of the OPO 18. In the alternative, one of the other cavity mirrors of the OPO 18 or may have an optimized reflectivity, thereby resulting in the idler being rejected by another cavity mirror. Those skilled in the art will appreciate that other mirrors within the OPO 18 and may have modified reflectivity coatings to shift the tuning range of the signal, thus shifting the tuning range of the idler. In a typical embodiment, the signal pulses can have average powers from about 50 mW to about 5 W, while the corresponding idler pulses can have average powers from about 50 mW to about 3 W.

Additional tuning ranges may be obtained through harmonic conversion of the signal or idler pulses. By way of illustration, as the signal tunes from about 650 nm to about 1400 nm the second harmonic of the signal will tune from about 325 nm to about 700 nm. Similarly a third harmonic signal may be generated and would tune from about 217 nm to about 467 nm. Likewise, a fourth harmonic signal may be generated and would tune from about 162 nm to about 350 nm. These harmonic signals may be generated in a nonlinear crystal which may include LBO, BBO, BiBO, PPSLT, PPKTP, CLBO, and KBBF. Additional tuning ranges can be produced by sum frequency mixing of the signal, idler or harmonics with the pump pulses at 1040 nm or the second harmonic of the pump pulses at 520 nm. This configuration can be advantageous since sum mixing with a high power beam can produce a higher output power. Finally, difference frequency mixing can be employed using any of the aforementioned sources to generate longer wavelength tunable output pulses. Wavelength as long as 10 to 12 microns can be generated in AgGaS and AgGaSe.

In the alternative, the signal and the idler may be separated in a Type I OPO using spatial separation. For example, the pulse of light from the pump source 14 and the OPO 18 may be positioned in a non-collinear geometry. As such, the pump signal 34 would be angularly displaced (i.e. less than 10 degrees) relative to the signal pulses generated within the OPO 18. As such, the direction of the idler pulses will be determined by phase matching and/or conservation of momentum. As the pump pulses and signal pulses are not aligned collinearly, the idler pulse will be emitted at an angle relative to the signal pulse, and, thus, may be removed spatially from the cavity.

In one embodiment, an angle tuned crystal may be used within the OPO 18. As shown in FIG. 3, the cavity formed within the OPO 18 needs to remain in alignment, including when the crystal is rotated. This crystal rotation may displace the intracavity beam. Optionally, a second crystal of equal length or a glass plate of an appropriate index of refraction may be used to compensate this displacement of the beam. In one embodiment, both crystals are placed between two curved cavity mirrors within the OPO 18 with the active crystal placed at the beam waist. Tuning is accomplished by rotating the active crystal in one direction. The compensator crystal or glass plate may then rotate in the opposite direction to maintain alignment of the intracavity beam.

The pulse duration of the optical signal 38 emitted from the OPO 18 may also depend on the total dispersion of the OPO 18. In one embodiment, chirped mirrors are used to generate the small amount of negative or positive dispersion needed to generate the shortest pulses. Optionally, any variety of devices may be used to generate the desired positive or negative dispersion, including, without limitations, matched mirror pairs, prisms, lenses, and the like. As such, the OPO 18 may include at least one dispersion compensation device therein. In one embodiment of an OPO 18 using mirrors with the broadest high reflection bandwidth, the dispersion will tend to vary periodically as a function of wavelength. As such, matched pairs of mirrors may be used to cancel these dispersion ripples. Optionally, the matched mirror pairs may be designed such that the maxima in the dispersion profiles of one mirror of the pair corresponds to minima in the dispersion profile of the other mirror of the pair, resulting in an overall flat dispersion profile. In one embodiment these paired mirrors can exhibit less than 400 $fs^2$ peak-to-valley dispersion ripples, while maintaining an average dispersion per pair within a couple of hundreds of $fs^2$ of 0 $fs^2$. Alternatively, the optimal dispersion can be obtained with an intracavity prism pair or sequence.

For the synchronously pumped OPO 18 to operate the repetition rate of the OPO 18 must match the repetition rate of the pump laser 14. The repetition rate may depend on the cavity length and thus the length of the cavity formed within the OPO 18 may be actively stabilized. In one embodiment, one or more servos, sensors, and the like may be used to detect the central wavelength emitted from the OPO 18. In another embodiment, the sensors may be used to detect the average power emitted from the OPO 18. Thereafter, the servos may be configured to adjust the cavity length within the OPO 18 in response to a signal from the sensors.

As shown in FIG. 1, a dispersion compensator 24 may be positioned between the broadly tunable ultrafast laser system 10 and the microscope 20. In one embodiment, the dispersion compensator 24 may comprise a folded pair of prisms, although those skilled in the art will appreciate that any variety of dispersion compensation devices may be used. Exemplary alternate dispersion compensators includes, without limitations, matched mirror pairs, prisms, gratings, prisms, Gires-Tournois interferometers, Dazzlers, electro-optic pulse shapers, and chirped mirrors. When the OPO 18 is tuned, the dispersion compensator 24 is configured to be adjusted to maintain the shortest pulse at the sample 22. In one embodiment, a control system 26 may be used for adjustment of the intracavity prism pair and the cavity length servo, the tuning of the crystal and compensator and the tuning of the dispersion compensator 24. Optionally, the dispersion compensator 24 may be positioned within the microscope 20, between microscope 20 and tunable ultrafast laser system housing 10 or within the broadly tunable ultrafast laser system housing 10. In another embodiment, the dispersion compensator 24 is positioned within the OPO 18. Further, the broadly tunable ultrafast laser system 10 may be operated without a dispersion compensator 24. As shown in FIG. 1, the dispersion compensator 28 outputs a compensated signal 40 to the microscope 20. For example, U.S. patent application Ser. No. 11/983,583, entitled Automatic Dispersion Compensation Over a Broad Wavelength Range for Coherent Optical Pulses, the entire contents of which are incorporated by reference herein, discloses a dispersion compensation scheme which may be used with the present system.

For many applications including multi-photon microscopy, it is desirable to maintain the beam pointing of the laser as the wavelength is tuned. At least one active mirror 50 may be used in conjunction with a quad cell or other detector to actively adjust the beam pointing. Optionally, a beam pointing servo may be used to keep the pointing of the output beam fixed both over time and as the wavelength is tuned. In another embodiment, a beam pointing servo is used to keep the pointing of the pump laser 14 fixed over time.

Figure 6:
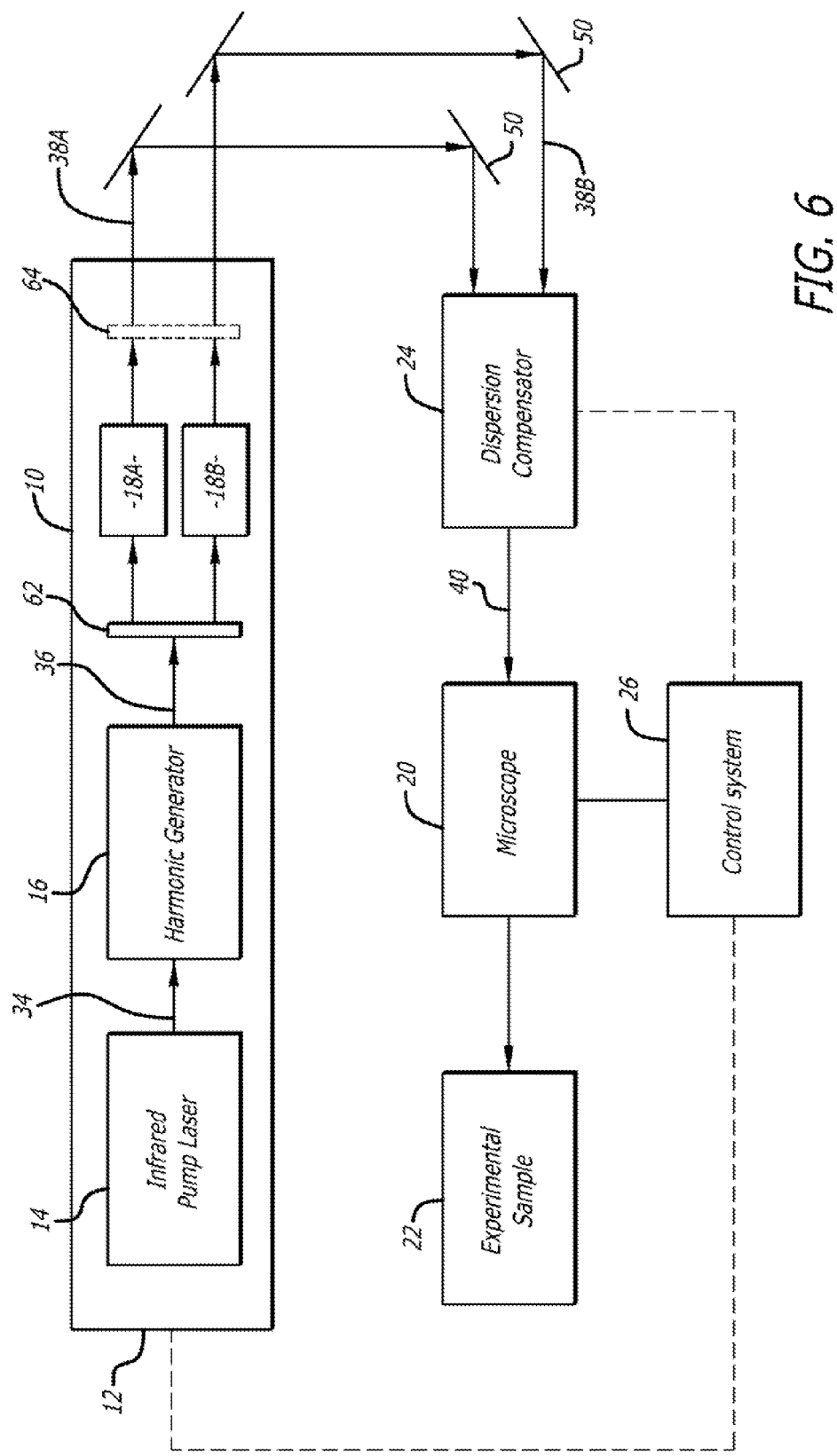
FIG. 6 shows a schematic diagram of another embodiment of a broadly tunable ultrafast laser system coupled to an optical system for examining an experimental sample.

Optionally, as shown in FIG. 6, in some applications it may be desirable to generate multiple synchronized and independently tunable ultrafast pulses. As such, at least one beam splitting device 62 may be used to split the harmonic output 36 that is output from the second harmonic generator 16 into multiple beams. As shown, each of these two beams can then pump an independent OPO 18A, 18B. The outputs 38A, 38B from each OPO 18A, 18B can then be independently tuned and the timing jitter between the output pulses may be substantially less than the duration of the pump pulses. Optionally, at least one additional optical component 64 may be used to condition the outputs of the individual OPOs 18A, 18B. For example, in one embodiment the optical component 64 comprises at least one beam combiner configured to combine the outputs 38A, 38B into a single output. In another embodiment, the outputs of the individual OPOs 18A, 188 may be used in individual microscope systems. As such, multiple dispersion compensators 24 may be used.

In addition, the pulse durations of the optical signal 38 may be selectively decreased or increased for a particular application. For example, for some application, such as seeding of amplifier systems, shorter duration signal and idler pulses are desirable. Optimal durations of the optical signal 38 can be in the range of about 10 fs to about 100 fs. Shorter pulse durations of these signals 38 may be accomplished by using shorter pump pulses, thinner OPO crystals with a correspondingly larger phase matching bandwidth, non-collinear phase matching, or improved group velocity dispersion matching. A further need is for these shorter duration pulses to have a stabilized carrier envelope phase. This can be accomplished by techniques known in the literature such as described in Gale et al., Optics Express 16, 1616 (2008), the contents of which are incorporated by reference herein.

In contrast, other applications may require the OPO 18 to generate longer pulses. For example, for CARS spectroscopy, transform limited picosecond pulses are desirable. In one embodiment, longer pulse durations may be accomplished by generating longer duration pump pulses. For example, modifying the pump laser 14 or increasing the length of the second harmonic generator 16 may result in longer pulse durations. One example of a modified pump laser 14 would use the gain media Nd:Vanadate. Additionally, the length of the crystal used within the OPO 18 may be increased and the value of the intracavity dispersion can be optimized to produce narrower bandwidth and thus generate transform limited pulses. Finally a narrower bandwidth may be generated by inserting at least one additional tuning element into the cavity of the OPO 18. Exemplary tuning elements include, without limitations, birefringent plates, etalons, volume Bragg gratings, gratings, prisms, grisms, and the like.

While particular forms of embodiments have been illustrated and described, it will be apparent that various modifications can be made without departing from the spirit and scope of the embodiments of the invention. Accordingly, it is not intended that the invention be limited by the forgoing detailed description

What is claimed is:

1. A laser system, comprising:
    at least one subpicosecond laser pump source configured to output at least one pump signal having a wavelength of about 650 nm or less;
    at least one type II optical parametric oscillator in optical communication with the pump source and configured to generate a single pulsed subpicosecond optical signal continuously tunable from about 650 nm to about 1400 nm;
    at least one optical system in optical communication with the optical parametric oscillator and configured to direct at least a portion of the optical signal to a specimen; and
    at least one analyzing device configured to receive at least one specimen signal from the specimen in response to the optical signal.

2. The device of claim 1 wherein the pump source comprises a diode pumped solid state laser system.

3. The device of claim 1 wherein the pump source includes at least one device selected from the group consisting of a bulk laser, a fiber laser, a fiber amplified bulk laser, a fiber amplifier, or a disk laser.

4. The device of claim 1 wherein the pump source comprises an infrared laser system configured to output a harmonic signal having a wavelength of 650 nm or less.

5. The device of claim 4 further comprising at least one harmonic generator in optical communication with the pump source and the optical parametric oscillator, the harmonic generator configured to receive the pump signal from the pump source and output the harmonic signal.

6. The device of claim 1 wherein the optical parametric oscillator includes at least one non-linear optical material.

7. The device of claim 6 wherein the optical parametric oscillator includes at least one optical crystal selected from the group consisting of LBO, BBO, BiBO, PPLN, PPSLT, PPKTP, KTiOPO$_4$, LiB$_3$O$_5$, and CsLiB$_6$O$_{10}$.

8. The device of claim 1 wherein the optical parametric oscillator includes at least one broadband minor.

9. The device of claim 1 wherein the optical parametric oscillator includes at least one component positioning device located therein.

10. The device of claim 9 wherein the component positioning system comprises a computer controlled positioning device.

11. The device of claim 9 wherein the component positioning system is configured to support at least one component selected from the group consisting of optical crystals, lenses, chirped mirrors, mirrors, output coupling mirrors, prisms, semiconductor saturable absorbers, broadband mirrors, and gratings.

12. The device of claim 1 wherein the laser system includes at least one dispersion compensation device.

13. The device of claim 12 wherein the dispersion compensation device is located within the optical parametric oscillator.

14. The device of claim 13 wherein the dispersion compensation device comprises at least one matched mirror pair.

15. The device of claim 12 wherein the dispersion compensation device is located outside the optical parametric oscillator.

16. The device of claim 15 wherein the dispersion compensation device is configured to receive the optical signal from the optical parametric oscillator and output a compensated optical signal to the optical system.

17. The device of claim 16 wherein the dispersion compensation device includes at least one device selected from the group consisting of prisms, gratings, grisms, Gires-Tournois interferometers, Dazzlers, electro-optic pulse shapers, and chirped mirrors.

18. The device of claim 1 further comprising a first optical parametric oscillator and a second optical parametric oscillator in communication with the laser pump source.

* * * * *